United States Patent [19]

Inukai et al.

[11] Patent Number: 5,116,544
[45] Date of Patent: May 26, 1992

[54] HEXAFLUORONEOPENTYL ALCOHOL, DERIVATIVE THEREOF FLUORINE-CONTAINING POLYMER AND ITS USE

[75] Inventors: Hiroshi Inukai; Takashi Yasuhara, both of Settsu; Takahiro Kitahara, Suita, all of Japan

[73] Assignee: Daikin Industries, Ltd., Osaka, Japan

[21] Appl. No.: 397,430
[22] PCT Filed: Dec. 5, 1988
[86] PCT No.: PCT/JP88/01228
§ 371 Date: Aug. 4, 1989
§ 102(e) Date: Aug. 4, 1989
[87] PCT Pub. No.: WO89/05287
PCT Pub. Date: Jun. 15, 1989

[30] Foreign Application Priority Data

Dec. 4, 1987 [JP] Japan ............... 62-308092
Dec. 10, 1987 [JP] Japan ............... 62-312529

[51] Int. Cl.$^5$ .................. C07C 69/62; C08F 18/20
[52] U.S. Cl. .................. 560/219; 560/223; 560/192; 560/197; 568/842; 526/245; 385/145
[58] Field of Search .................. 560/223, 219; 526/245

[56] References Cited

FOREIGN PATENT DOCUMENTS

59/21648 2/1984 Japan .

*Primary Examiner*—Paul J. Killos
*Attorney, Agent, or Firm*—Larson and Taylor

[57] ABSTRACT

This invention provides (i) novel hexafluoroneopentyl alcohol, (ii) its derivatives, i.e., hexafluoroneopentyl (meth)acrylate, (iii) fluorinated polymers comprising said acrylate as the monomer component, and (iv) optical materials comprising said fluorinated polymers.

4 Claims, No Drawings

HEXAFLUORONEOPENTYL ALCOHOL, DERIVATIVE THEREOF FLUORINE-CONTAINING POLYMER AND ITS USE

FIELD OF THE INVENTION

The present invention relates to a novel hexafluoroneopentyl alcohol, hexafluoroneopentyl acrylate or methacrylate obtained as its derivative, fluorine-containing polymer prepared from the derivative and the use of the polymer as an optical material.

PRIOR ART AND ITS PROBLEMS

Optical fibers are well known which comprise a transparent glass or plastics core and a cladding covering the core concentrically therewith to provide a composite fiber and having a lower refractive index than the core material, such that when light is applied at one end of the fiber, light travels through the fiber while being totally reflected in its interior.

Various polymers have been proposed for use as plastics materials for forming a cladding. Of these polymers, only a few are fully satisfactory in the properties of having a high softening temperature and a low refractive index which are required of cladding materials for optical fibers. Of the few, perfluoro-t-butyl methacrylate is disclosed in Japanese Unexamined Patent Publication No. 49-129,545 as optical materials capable of fulfilling said property requirements.

However, perfluoro-t-butyl methacrylate has the drawbacks of having a low flexibility and a poor adhesion to the core.

An object of the present invention is to provide a novel monomer compound and a starting material for the monomer compound, the monomer compound being capable of giving a polymer which is free of the foregoing drawbacks, namely fully satisfactory in the properties of having a high softening temperature and a low refractive index as required of cladding materials for optical fibers and excellent in the flexibility and good in the adhesion to the core.

MEANS FOR SOLVING THE PROBLEMS

The present inventors discovered that a polymer prepared from hexafluoroneopentyl acrylate or methacrylate which is a novel monomer compound has a specifically high glass transition temperature (hereinafter referred to as "Tg"), a low refractive index, a great flexibility and a good adhesion to the core and that the hexafluoroneopentyl acrylate or methacrylate can be easily synthesized from a novel hexafluoroneopentyl alcohol. The present invention has been accomplished based on these novel findings.

According to the present invention, there are provided a hexafluoroneopentyl alcohol represented by the formula

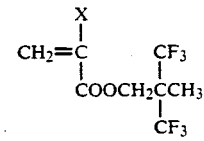

and hexafluoroneopentyl acrylate or methacrylate represented by the formula

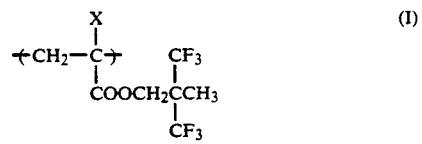

wherein X represents hydrogen atom, fluorine atom, chlorine atom, bromine atom, iodine atom or methyl group.

According to the present invention, there are further provided a fluorine-containing polymer comprising a structural unit represented by the formula $$\begin{array}{c} X \\ | \\ \text{-(CH}_2\text{-C)-} \quad \text{CF}_3 \\ | \quad | \\ \text{COOCH}_2\text{CCH}_3 \\ | \\ \text{CF}_3 \end{array} \quad (I)$$

wherein X represents hydrogen atom, fluorine atom, chlorine atom, bromine atom, iodine atom or methyl group, and an optical material prepared from said fluorine-containing polymer.

The hexafluoroneopentyl alcohol of this invention can be prepared by the following process. First, as illustrated in the following reaction scheme, an adduct of octafluoroisobutene with methanol (a) is subjected to a reaction for removing HF, giving the olefin (b) shown below. The olefin (b) is subjected to rearrangement reaction, giving the acid fluoride (c) shown below which is then subjected to reduction.

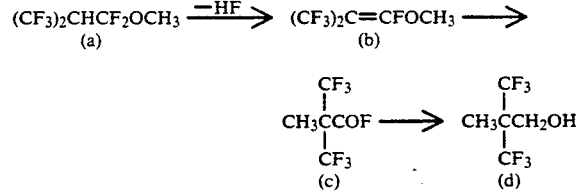

The foregoing rearrangement reaction is conducted in the presence of a suitable solvent. Examples of preferred solvents are dimethylformamide, dimethylacetoamide, etc. The amount of the solvent used is 0.01 to 10 times, preferably 0.1 to 2 times, the amount of the olefin (b). A smaller amount of the solvent used reduces the rate of rearrangement reaction, whereas a larger amount thereof involves a cumbersome treatment of waste and leads to formation of reaction product in a small amount despite the large reaction scale. A preferred reaction temperature is in the range of room temperature to 100° C.

The reduction from the acid fluoride (c) to the product (d) is carried out using a reducing agent in an organic solvent. Examples of useful organic solvents are diethyl ether, diglyme, tetrahydrofuran, etc. Examples of useful reducing agents are LiAlH$_4$, NaBH$_4$, etc. The amount of the organic solvent used is 1 to 10 times the amount of the acid fluoride (c) and the amount of the reducing agent used is 0.5 to 5 moles per mole of the acid fluoride (c). A preferred reaction temperature is 40° to 150° C. The reduction may be performed directly by using H$_2$.

The obtained hexafluoroneopentyl alcohol (d) is purified preferably by distillation. The hexafluoroneopentyl alcohol (d) of the invention is in the form of colorless needle-like crystals at room temperature.

Next, the process for preparing the hexafluoroneopentyl acrylate or methacrylate of the invention will be described below. The hexafluoroneopentyl acrylate or methacrylate is prepared by one of the following processes (1) to (3) using as the starting compound the hexafluoroneopentyl alcohol given by the foregoing process; (1) subjecting the hexafluoroneopentyl alcohol to dehydrohalogenation reaction with acrylic or methacrylic acid halide in the presence of a co-acid catalyst such as pyridine, triethylamine or like organic base, (2) subjecting the hexafluoroneopentyl alcohol to dehydration reaction with acrylic or methacrylic acid using a dehydrating agent such as phosphorus pentoxide, sulfuric acid or the like and (3) subjecting the hexafluoroneopentyl alcohol to ester interchange reaction with methyl acrylate or methacrylate.

Of the processes (1) to (3), the processes (1) and (2) are more preferred in view of ease of operation and yield. When required, a solvent such as benzene, toluene, dimethylformamide or the like may be used in these reactions. In the process (1), the amount of the co-acid catalyst used is 0.1 to 2 moles per mole of the hexafluoroneopentyl alcohol and a preferred reaction temperature is 0° to 100° C. In the process (2), the amount of the dehydrating agent used is 0.7 to 5 moles per mole of the hexafluoroneopentyl alcohol and a preferred reaction temperature is 50° to 100° C.

When a readily polymerizable monomer compound is produced, the reaction is done in the presence of a polymerization inhibitor. Useful polymerization inhibitors are not specifically limited insofar as they can inhibit radical polymerization. Examples of such polymerization inhibitors are hydroquinone, hydroquinonemonomethyl ether, tri-tert-butyl phenol, tert-butyl catechol, phenothiazine, etc.

The hexafluoroneopentyl acrylate or methacrylate of the invention is a colorless, transparent liquid at room temperature.

The fluorine-containing polymers of the invention include not only homopolymers having the structural unit of the formula (I) but copolymers containing 10% by weight or more of the structural unit of the formula (I).

Examples of preferable copolymers include those comprising 10% by weight or more of the structural unit of the formula (I) and 90 to 0.1% by weight, preferably 70 to 0.1% by weight, more preferably 50 to 0.1% by weight, of a structural unit represented by the formula

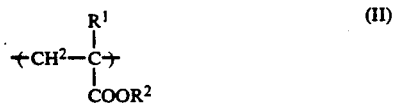

(II)

wherein $R^1$ represents hydrogen atom, fluorine atom or methyl group, and $R^2$ represents hydrogen atom, lower alkyl group or fluoroalkyl group.

X in the formula (I) is preferably fluorine atom or methyl group. In the formula (II), $R^1$ is preferably fluorine atom or methyl group, and $R^2$ is preferably aliphatic group such as —CH$_3$, —CH$_2$CH$_3$, —CH$_2$CH$_2$CH$_3$ and the like, alicyclic hydrocarbon group such as

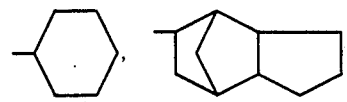

and the like, and fluoroalkyl group such as —CH$_2$CF$_3$, —CH$_2$CF$_2$CF$_2$H, —CH$_2$CF$_2$CFHCF$_3$, CH$_2$CH$_2$C$_8$F$_{17}$ and the like. $R^2$ may contain functional group such as —CH$_2$CH$_2$OH, —CH$_2$CH$_2$CH$_2$Si(OCH$_3$)$_3$, —H, —CH$_2$CHCH, etc.

The polymer of the invention may be a copolymer prepared by copolymerizing said monomer with other monomers such as styrene, vinyl chloride or the like insofar as such monomers do not impair the characteristics of the resulting copolymer.

The fluorine-containing polymer of the invention can be prepared by homopolymerizing the hexafluoroneopentyl acrylate or methacrylate or copolymerizing the monomer with other monomers.

The fluorine-containing polymer of the invention is prepared by a usual mode of polymerization such as mass (or bulk) polymerization, solution polymerization, suspension polymerization or emulsion polymerization.

Preferred polymerization initiators for use in preparation of the fluorine-containing polymer by mass (or bulk), solution or suspension polymerization are azobisisobutyronitrile, isobutyryl peroxide, octanoyl peroxide, diisopropyl peroxy dicarbonate, fluorine-containing organic peroxides represented by the formula [Cl(CF$_2$CFCl)$_2$CF$_2$COO]$_2$, [X(CF$_2$CF$_2$)$_n$COO]$_2$ and [X(CF$_2$CF$_2$)$_n$COO]$_2$ (in the formulae, X is hydrogen, fluorine or Cl, and n is 1 to 10], etc. Polymerization initiators useful for emulsion polymerization are redox initiators including oxidizing agents such as ammonium persulfate, potassium persulfate and like persulfates, reducing agents such as sodium sulfite, and salts of transition metals such as ferrous sulfate.

It is desirable in the mass, solution or suspension polymerization to use a chain transfer agent such as mercaptans in order to provide the novel fluorine-containing polymer with a higher thermal decomposition temperature and to adjust the molecular weight distribution. When a chain transfer agent is used, the amount of the agent used, is 0.01 to 1 part by weight per 100 parts by weight of the monomer.

Typical of the media useful in preparing the novel fluorine-containing polymer of the invention by the solution or suspension polymerization are Freon-12, Freon-113, Freon-114, Freon-C318 and like fluorine-type solutions and hydrocarbon solvents such as butyl acetate, methyl isobutyl ketone and the like.

The polymerization temperature, which is usually in the range of 0° to 100° C., is determined in connection with the decomposition temperature of the polymerization initiator used. Preferably the temperature is 10° to 80° C. in most cases.

The polymerization pressure ranges from 0 to 50 kg/cm$^2$G.

The fluorine-containing polymers of the invention which can be prepared by the foregoing polymerization reaction are usually about 10,000 to about 5,000,000 in molecular weight (as determined by gel permeation chromatography), about 0.15 to about 3.0 in viscosity [η] as determined at 35° C. with MEK, 1.37 to 1.45 in refractive index ($n_d^{25}$) and 120° to 160° C. in glass transition temperature.

The novel fluorine-containing polymers of the invention have a higher glass transition temperature than fluoroalkyl methacrylate polymers usually used as a plastics cladding material for optical fibers and therefore can be used in a situation at a comparatively high temperature, for example in the vicinity of an engine of a vehicle where conventional plastics cladding materials can not be used. With a high decomposition temperature, the polymers of the invention have the further advantage of facilitating control of the temperature for fusing the polymer since a wide range of heating temperature is available in fusing and spinning for production of optical fibers.

Further, the fluorine-containing polymers of the invention have a low refractive index, a high transparency and a good flexibility, hence excellent as an optical material.

The polymers of the invention have other applications for optical fibers than as the plastics cladding material for optical fibers. For example, the polymers of the invention can be used as a coating agent for preventing reflection of light beams which is applied to the surface of a substrate such as plastics, glass or the like to prevent the undesired glare or light scattering.

In addition to applications as optical materials, the polymers of the invention are also usable as an organic glass and an additive for weather-resistant coating compositions.

EXAMPLES

The features of the present invention will be clarified below in more detail with reference to the following Examples and Comparative Examples.

EXAMPLE 1

Into a 1-l, four-necked glass flask equipped with a thermometer, a dropping funnel, a stirrer and a reflux condenser were placed 133.37 g (0.6 mol) of tetraglyme and 15.13 g (0.4 mol) of sodium boron hydride and the mixture was maintained at a temperature of 80° C. To the mixture was added dropwise 106.04 g (0.5 mol) of 2,2-bis(trifluoro)propionic fluoride over a period of 2.5 hours. After addition, the mixture was stirred at 80° C. for 3 hours and then cooled to 20° C. Subsequently, 21 cc of hydrochloric acid (35%) was added dropwise thereto and the resulting mixture was washed with 500 cc of water and thereafter distilled at normal pressure, giving 60 g of hexafluoroneopentyl alcohol having a boiling point of 110° C. (yield: 60%). The obtained product consisted of colorless, needle-like crystals. The identification was carried out with $^{19}$F-NMR spectrum and $^1$H-NMR spectrum. The spectrum was determined with use of a nuclear magnetic resonance spectrometer (Model FX-100, manufactured by JEOL. Ltd.)

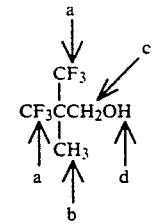

| No. | δ (ppm) |
|---|---|
| $^{19}$F-NMR (CF$_3$COOH standard) | |
| a | 7.2 |
| $^1$H-NMR (TMS standard) | |
| b | 1.36 |
| c | 3.90 |
| d | 3.17 |

EXAMPLE 2

Into a 500-ml glass flask were placed 150 g (0.765 mol) of hexafluoroneopentyl alcohol obtained in Example 1, 73 g (0.85 mol) of methacrylic acid and 1 g of t-butyl catechol and the mixture was heated to 70° to 80° C. Then 50 g of diphosphorus pentoxide was added over a period of 2 hours. In this step, the temperature was maintained at 80° to 90° C. After addition, the mixture was further kept at 80° to 90° C. for 3 hours to complete the reaction. The reaction mixture was washed with 300 ml of water and the resulting hexafluoroneopentyl methacrylate was distilled under a reduced pressure of 15 mm·Hg. The obtained product had a boiling point of 55° C. and a purity, determined by gas chromatography, of 99.9%. The identification was conducted with $^1$H-NMR spectrum, $^{19}$F-NMR spectrum and $^{13}$C-NMR spectrum (in every case, solvent: acetone-d$_6$).

In respect of the compound represented by the formula

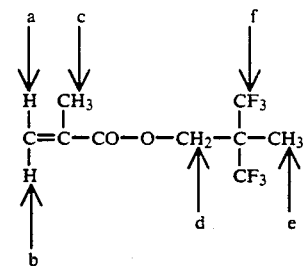

there were determined the following chemical shift (δ) and coupling constant (J).

| No. | δ (ppm) | J (Hz) | coupling form |
|---|---|---|---|
| $^1$H-NMR (TMS standard) | | | |
| a | 5.67 | — | m |
| b | 6.16 | — | m |
| c | 1.92 | 2.1 | d-d |
| d | 4.50 | — | s |
| e | 1.50 | — | s |
| $^{19}$F-NMR (CF$_3$COOH standard) | | | |
| f | 5.8 | — | s |
| $^{13}$C-NMR | | | |

-continued

| No. | δ (ppm) | J (Hz) | coupling form |
|---|---|---|---|

$$\underset{A}{\overset{H}{\underset{H}{\phantom{|}}}}\overset{C}{\underset{\phantom{|}}{C}}=\overset{CH_3}{\underset{B}{C}}-\overset{\phantom{|}}{\underset{D}{CO}}-O-\overset{\phantom{|}}{\underset{E}{CH_2}}-\overset{CF_3}{\underset{\underset{G}{CF_3}}{C}}-\overset{\phantom{|}}{\underset{H}{CH_3}}$$

TMS standard

| | |
|---|---|
| A | 126.3 |
| B | 136.0 |
| C | 17.7 |
| D | 165.80 |
| E | 61.3 |
| F | 51.1 |
| G | 125.3 |
| H | 12.2 |

(Note)
s: singlet
d: doublet
m: multiplet
Low magnetic field: +

EXAMPLE 3

Into a 200-ml, four-necked glass flask provided with a thermometer, a dropping funnel, a stirrer and a reflux condenser were placed 58.83 g (0.3 mol) of hexafluoroneopentyl alcohol, 30.36 g (0.3 mol) of triethylamine and 50 g of chloroform. Subsequently, to the mixture was added dropwise 30.37 g (0.33 mol) of 2-fluoroacrylic fluoride at a temperature of up to 10° C. with ice-cooling. After addition, the mixture was stirred at room temperature for 30 minutes. The mixture was washed with an aqueous solution of sodium bicarbonate (5%) and then with pure water, followed by evaporation to remove chloroform, producing hexafluoroneopentyl acrylate. The amount of the obtained product was 67.17 g and the yield was 76.7%. To the product was further added 0.1 g of t-butyl catechol as a polymerization inhibitor and the mixture was distilled under reduced pressure for purification. The boiling point was 55° to 56° C./20 mm·Hg. The identification was performed with $^1$H-NMR spectrum, $^{19}$F-NMR spectrum and $^{13}$C-NMR spectrum (in every case, sovent: acetone-$d_6$).

$$\underset{\underset{b}{\uparrow}}{\overset{a\;\;\;e}{\underset{\phantom{|}}{\downarrow\;\downarrow}}}\overset{H}{\underset{H}{\phantom{|}}}\overset{F}{\underset{\phantom{|}}{\phantom{|}}}C=C-CO-O-\overset{\overset{c}{\downarrow}}{CH_2}-\overset{CF_3}{\underset{CF_3}{\overset{\overset{d}{\downarrow}}{C}}}-CH_3$$

$^1$H-NMR (TMS standard)

| No. | δ (ppm) |
|---|---|
| a | 5.72 |
| b | 5.44 |
| c | 4.54 |
| d | 1.47 |

| No. | J (Hz) |
|---|---|
| Ja-b | 4 |
| Ja-e | 43 |
| Jb-e | 13 |

$^{19}$F-NMR (CF$_3$COOH standard)

| No. | δ (ppm) |
|---|---|
| e | −40.2 |
| f | +5.9 |

$^{13}$C-NMR $$A\to\overset{H}{\underset{H}{\phantom{|}}}\overset{F}{\underset{\phantom{|}}{C}}=\overset{\phantom{|}}{\underset{\phantom{|}}{C}}-CO-O-CH_2-\overset{CF_3}{\underset{\underset{F}{\uparrow}}{\underset{CF_3}{C}}}-CH_3$$

| | |
|---|---|
| A | 103.9 |
| B | 153.1 |
| C | 159.4 |
| D | 62.4 |
| E | 51.3 |
| F | 125.0 |
| G | 12.5 |

Low magnetic field: +

EXAMPLE 4

Into a 500-ml glass flask were placed 100 parts of hexafluoroneopentyl methacrylate which was purified by distillation under reduced pressure, 0.05 part of n-dodecyl mercaptan, a polymerization initiator and 0.025 part of 2,2'-azoisobutylonitrile. These substances were mixed for dissolution and a cycle of deaeration and substitution with nitrogen was repeated for hermetically sealing the mixture in the flask.

Subsequently, the mixture was polymerized for 16 hours in a reactor maintained at a temperature of 70° C. After completion of the polymerization, to the obtained polymer was added 300 g of acetone for dissolution and the solution obtained was poured into 5 l of methanol. The precipitated polymer was separated from the liquid and dried at 100° C. under reduced pressure for 10 hours to prepare 96.2 g of a polymer (yield: 96%). With respect to molecular weight, the polymer obtained was found to have an inherent viscosity [η] of 0.596 at 35° C. using MEK. The polymer was identified with elemental analysis and nuclear magnetic resonance spectrum. The result of the elemental analysis was C: 40.9, H: 3.8, F: 43.2 and O: 12.1 (%). The nuclear magnetic reasonance spectrum was as follows.

$$-CH_2-\overset{\overset{b}{\downarrow}}{\underset{\phantom{|}}{\underset{\phantom{|}}{C}}}\overset{CH_3}{\underset{\phantom{|}}{\phantom{|}}}-\underset{\underset{c}{\uparrow}}{\phantom{|}}\phantom{-}\\ \phantom{-CH_2-C-}CO-O-CH_2-\overset{CF_3}{\underset{CF_3}{C}}-CH_3$$

$^1$H-NMR (TMS standard)

| No. | δ (ppm) |
|---|---|
| a | 1.6–2.4 |
| b | 1 |
| c | 4.26 |

-continued

| | |
|---|---|
| d | 1.55 |

¹⁹F-NMR (CF₃COOH standard)

| | |
|---|---|
| e | +6.4 |

¹³C-NMR

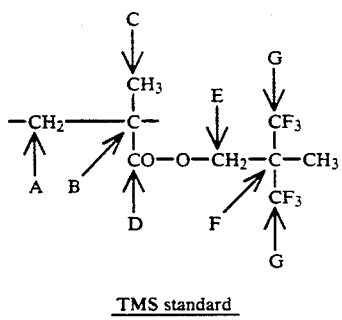

TMS standard

| | |
|---|---|
| A | 50–52 |
| B | 45.0 |
| C | 16.7, 18.3 |
| D | 175.2, 175.9, 176.2 |
| E | 62.6 |
| F | 50.3 |
| G | 124.7 |
| H | 12.4 |

Low magnetic field: +

EXAMPLE 5

Into a 500-ml glass flask were placed 100 parts of hexafluoroneopentyl-α-fluoroacrylate which was purified by distillation under reduced pressure, 0.025 part of n-dodecyl mercaptan, 1.0 part of 2,2′-azobisisobutylonitrile and 233 parts of ethyl acetate serving as a solvent for polymerization. The aforementioned substances were mixed for dissolution and a cycle of deaeration and substitution with nitrogen was repeated for hermetically sealing the mixture in the flask.

Then the mixture was subjected to polymerization for 18 hours in a reactor maintained at a temperature of 50° C. After completion of the polymerization, the obtained solution of the polymer was poured into 5 l of methanol. The precipitated polymer was separated from the liquid and dried under reduced pressure at 100° C. for 10 hours to produce 93 g of a polymer (yield: 93%). In respect of molecular weight, the polymer produced was found to have an inherent viscosity [η] of 0.423 at 35° C. using MEK. The identification of the polymer was carried out with elemental analysis and nuclear magnetic resonance spectrum.

The result of the elemental analysis was C: 35.8%, H: 2.6%, F: 49.6% and O: 11.9%. The nuclear magnetic resonance spectrum was as follows.

| No. | δ (ppm) |
|---|---|

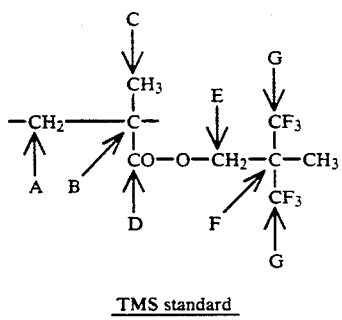

¹H-NMR (TMS standard)

| | |
|---|---|
| a | 2.0–3.32 |

| No. | δ (ppm) |
|---|---|
| b | 4.42 |
| c | 1.54 |

¹⁹F-NMR (CF₃COOH standard)
Low magnetic field: +

| | |
|---|---|
| d | 85.2, 88.8, 93.5 |
| e | −6.2 |

¹³C-NMR

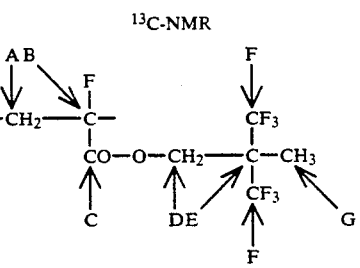

TMS standard

| | |
|---|---|
| A | 44.7 |
| B | 92.1 |
| C | 169.0, 167.9, 166.8 |
| D | 62.0 |
| E | 50.6 |
| F | 124.6 |
| G | 11.8 |

EXAMPLE 6

Into a 500-ml glass flask were placed 90 parts of hexafluoroneopentyl methacrylate which was purified by distillation under reduced pressure, 10 parts of methyl methacrylate, 0.1 part of n-dodecyl mercaptan and 0.025 part of 2,2′-azobisisobutylonitrile. These substances were mixed for dissolution and the obtained mixture was polymerized in the same manner as in Example 1, giving 98.5 g of a polymer (yield: 98.5%).

In respect of molecular weight, the obtained polymer was found to have an inherent viscosity [η] of 0.494 at 35° C. using MEK. Further the identification of the polymer was effected with elemental analysis and nuclear magnetic reasonance spectrum.

The result of the elemental analysis was C: 42.8%, H: 4.2%, F: 38.9% and O: 14.1%.

The nuclear magnetic resonance spectrum was as follows.

| No. | δ (ppm) |
|---|---|

¹H-NMR (TMS standard)

| | |
|---|---|
| a, e | 1.6–2.4 |
| b, f | 1 |
| c | 4.32 |
| d | 1.60 |
| g | 3.60 |

¹⁹F-NMR (CF₃COOH standard) Low magnetic field: +

| | |
|---|---|
| h | +6.6 |

-continued

| No. | δ (ppm) |
|---|---|

13C-NMR

```
         C                        K
     A B ↓                        ↓
      ↘↙ CH3                      CH3
  -CH2-C-           -CH2-C-
         |              G    ↑ ↑
         |              ↓    I  J
         |              CF3
         CO-O-CH2-C-CH3       COOCH3
         ↑   ↑  ↑   |         ↑   ↑
         D   E     CF3        L   M
                   ↑
                   G
```

TMS standard

| A, I | 53.8 |
| B, J | 44.6, 44.9 |
| C, K | 16.4, 18.3 |
| D, L | 175.2–177.4 |
| E | 62.5 |
| F | 50.3 |
| G | 124.0 |
| H | 12.4 |
| M | 51.4 |

EXAMPLE 7

Into a 500-ml glass flask were introduced 90 parts of hexafluoroneopentyl-α-fluoroacrylate which was purified by distillation under reduced pressure, 10 parts of methyl-α-fluoroacrylate, 1.0 part of n-dodecyl mercaptan and 0.1 part of 2,2′-azobisisobutylonitrile. These substances were mixed for dissolution and the resulting mixture was polymerized in the same manner as in Example 1 (except that, in this case, the polymerization was conducted at a temperature of 50° C.), producing 98.3 g of a polymer (yield: 98.3%).

With regard to molecular weight, the polymer thus obtained was found to have an inherent viscosity [η] of 0.621 at 35° C. using MEK.

The result of the elemental analysis was C: 36.85%, H: 2.8%, F: 46.5%, and O: 13.8%.

The nuclear magnetic resonance spectrum was as follows.

| No. | δ (ppm) |
|---|---|

```
     f             h
     ↓             ↓
     F             F
  a  |          d  |
  ↓  |          ↓  |
  -CH2-C-       -CH2-C-
       |             |
       |             COOCH3
       |             ↑
       |             e
       CF3
       |
       CO-O-CH2-C-CH3
              ↑  |  ↑
              b  CF3 c
                 ↑
                 g
```

1H-NMR (TMS standard)

| a, d | 2.0–3.34 |
| b | 4.42 |
| c | 1.55 |
| e | 3.70 |

19F-NMR (CF3COOH standard)

| No. | δ (ppm) |
|---|---|
| | Low magnetic field: + |
| f, h | 85.2, 88.8, 93.4 |
| g | −6.2 |

13C-NMR

```
          H             I
          ↓       F     ↓
          F       |  F
  -CH2-C-    -CH2-C-
       ↑↖          ↑ ↑
       A  B        COOCH3
          ↓      CF3 E  J  K
          D       ↘↙
          CO-O-CH2-C-CH3
          ↑   ↑      ↘
          C   D      G
                  CF3
                  ↑
                  F
```

TMS standard

| A, H | 44.3 |
| B, I | 92.1 |
| C, J | 169.0, 167.9, 166.8 |
| D | 62.0 |
| E | 50.6 |
| F | 124.6 |
| G | 11.8 |
| K | 52.2 |

COMPARATIVE EXAMPLE 1

The polymer of Comparative Example 1 was prepared in the same manner as in Example 4 with the exception of using 2,2,3,3-tetrafluoropropyl methacrylate in place of hexafluoroneopentyl methacrylate.

COMPARATIVE EXAMPLE 2

The polymer of Comparative Example 2 was prepared in the same manner as in Example 4 with the exception of using perfluoro-t-butyl methacrylate in lieu of hexafluoroneopentyl methacrylate.

TEST EXAMPLE 1

The polymers of the present invention as obtained in Examples 4 to 7 were checked for the following properties. Table 1 shows the results. Properties were evaluated according to the following methods.

(1) Glass Transition Temperature (Tg)

Using a differential scanning calorimeter (Model DSC II, manufactured by Perkin Elmer Co.), the temperature at which the polymer started to absorb heat was determined while elevating the temperature at a rate of 20° C./min.

(2) Decomposition Temperature (Tn)

Using a differential scanning calorimeter (Model DTG-30, manufactured by Shimadzu Seisakusho, Ltd.), the temperature at which the polymer started to decrease weight was determined while heating the polymer at a temperature elevating rate of 10° C./min.

(3) Refractive Index ($n_D$)

Measured at 25° C. with use of Abbe refractometer (manufactured by Atago Kogakukiki Mfg. Co., Ltd.).

(4) Melt Index (MI)

Using a Koka flow tester, manufacture by Shimadzu Seisakusho, Ltd., the fluorine-containing polymer of the present invention was placed into a cylinder having an inside diameter of 9.5 mm, maintained at 230° C. for 5 minutes and thereafter extruded through a nozzle having a length of 8 mm and an inside diameter of 2.1 mm under a piston load of 7 kg. The amount in gram of the polymer extruded for a period of 10 minutes was measured as MI.

(5) Transmission (Tm)

An optical fiber, 300 μm in diameter (15 μm in wall thickness of the cladding material) and 500 mm in length, was conjugate spun at 230° C. with use of polymethylmethacrylate as the core material and the fluorine-containing polymer of the invention as the cladding material. The transmission was measured with light 650 to 680 nm in wavelength.

(6) Flexibility (Fb)

The fluorine-containing polymer according to the invention was made into a fiber having a diameter of 1 mm by the same method as used for measuring MI. The fiber was wound around round steel rods at room temperature to determine the radius of the rod on which cracks developed in the fiber.

TABLE 1

| Ex. No. | Tg (°C.) | Tn (°C.) | $n_D$ | MI | Tm (%) | Fb (mm) |
|---|---|---|---|---|---|---|
| 4 | 150 | 286 | 1.395 | 30 | 80 | 15 |
| 5 | 135 |  | 1.37 | 78 | 84 | <6 |
| 6 | 140 | 283 | 1.41 | 50 | 75 | 10 |
| 7 | 150 |  | 1.38 | 33 | 78 | <6 |

TEST EXAMPLE 2

Even when the polymer obtained in Example 4 was left to stand in an atmosphere at 85° C. for 100 hours, there was no decrease in transmission.

TEST EXAMPLE 3

The materials used in Example 6 were dissolved in ethyl acetate to a concentration of 5% by weight and the solution was applied to a PMMA plate (trade name: "Acrypet", product of Mitsubishi Rayon Co., Ltd.) with a doctor blade, 250 μm in length. The coated plate was dried at 80° C. for 1 hour to produce a specimen plate. The thickness of the coat was 8 μm. The properties of the specimen plate were evaluated according to the following test methods.

(1) Reflectance

With an UV spectrometer (Model U3200, manufactured by Hitachi, Ltd.) equipped with 5 degrees-specular reflection apparatus, an average reflectance of the coated plate was determined with light of 400 to 700 nm in wavelength.

(2) Abrasion Resistance

Using a rubbing tester, manufactured by Taihei rika Kabushiki Kaisha, in which a fabric made of Tetoron (brand name of a polyester resin) was set, the coated plate was rubbed with the fabric 1000 times under the weight of 500 g.

(3) Adhesion

Cross-cut/cellophane adhesive tape peeling test was carried out according to JIS K5400.

As a result, the reflectance was up to 2.0% and the abrasion resistance was satisfactory.

The coated MMA plate was 85% in transmission with light having a wavelength of 400 to 700 nm. The result of the adhesion (cross-cut) test was 100/100. When the same experiments were conducted at a temperature of 80° C., the results were not different.

COMPARATIVE TEST EXAMPLE 1

The softening temperature and the decomposition temperature of the polymer of Comparative Example 1 were as low as 72° C. and 265° C., respectively and the refractive index was 1.42.

An optical fiber was spun at 250° C. with use of the foregoing polymer of Comparative Example 1 as the cladding material and polymethylmethacrylate as the core material to find formation of voids in the cladding. At 210° C., spinning could not be effected owing to clogging of nozzle. The optical fiber similar to those obtained in Examples was produced only when the spinning was performed at 230° C., and the transmission of the obtained fiber was 76%. However, the transmission of the fiber was reduced to 52% when the fiber was allowed to stand in an atmosphere at 85° C. for 100 hours.

The polymer prepared in Comparative Example 1 was applied to a PMMA plate by the same procedure as in Test Example 3 to produce a specimen plate.

The coated plate thus obtained had a reflectance of as low as 2.5% and was found to receive a number of scratches when rubbed 50 times, hence unsatisifactory in abrasion resistance.

In the case where the same experiment for checking the abrasion resistance was performed at a temperature of 80° C., the coated plate was found to receive a lot of scratches when rubbed twice.

COMPARATIVE TEST EXAMPLE 2

The polymer of Comparative Example 2 was found, as a result of the measurement, to be not less than 30 nm in flexibility (Fb), hence unusable.

Further, the polymer of the Comparative Example 2 was dissolved in 1,1,2-trichloro-2,2-trifluoroethane to a concentration of 5% and the solution was applied to a PMMA plate in the same manner as in Test Example 3 to form a coat having a thickness of 8 μm.

The coat thus formed was checked for adhesion to result in 0/100 by only one peeling trial of the adhesive tape.

We claim:

1. A hexafluoroneopentyl (meth)acrylate represented by the formula

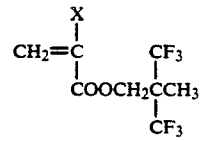

wherein X represents hydrogen atom, fluorine atom, chlorine atom, bromine atom, iodine atom or methyl group.

2. A hexafluoroneopentyl (meth)acrylate according to claim 1 wherein X is fluorine atom or methyl group.

3. A fluorine-containing polymer comprising a structural unit represented by the formula

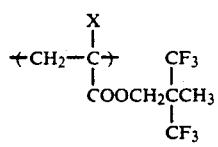 (I)

wherein X represents hydrogen atom, fluorine atom, chlorine atom, bromine atom, iodine atom or methyl group.

4. A fluorine-containing polymer according to claim 3 which comprises 10 to 99.9% by weight of the structural unit represented by the formula (I) and 0.1 to 90% by weight of the structural unit represented by the formula

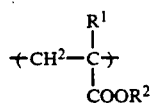 (II)

wherein $R^1$ represents hydrogen atom, fluorine atom or methyl group, and $R^2$ represents hydrogen atom, lower alkyl group or fluoroalkyl group.

* * * * *